(12) United States Patent
Vaupel

(10) Patent No.: US 6,545,029 B2
(45) Date of Patent: Apr. 8, 2003

(54) PHENYLSERINE DERIVATIVES AS INTEGRIN ANTAGONISTS

(75) Inventor: Andrea Vaupel, Riehen (CH)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/879,483

(22) Filed: Jun. 12, 2001

(65) Prior Publication Data

US 2002/0095050 A1 Jul. 18, 2002

Related U.S. Application Data

(60) Provisional application No. 60/211,041, filed on Jun. 12, 2000.

(51) Int. Cl.$^7$ .................... A61K 31/44; A61K 31/24; C07D 213/53; C07C 229/00; C07C 275/00
(52) U.S. Cl. .................. 514/357; 560/34; 560/45; 562/439; 562/444; 546/332; 514/534; 514/538; 514/539; 514/567
(58) Field of Search ............... 560/34, 45; 562/439, 562/444, 448; 546/332; 514/534, 538, 539, 567, 357

(56) References Cited

U.S. PATENT DOCUMENTS 6,313,119 B1 * 11/2001 Peyman et al.

FOREIGN PATENT DOCUMENTS

| WO | WO 96/15096 A1 * | 5/1996 |
| WO | 9724119 | 10/1997 |
| WO | 9818461 | 7/1998 |
| WO | 0006169 | 10/2000 |

OTHER PUBLICATIONS

Brooks, P. C., Stromblad, S., Klemka, R., Visscher, D., Sarkar, F. H., and Cheresch, D. A., "Antiintegrin αvβ3 blocks human breast cancer growth and angiogenesis in human skin", J. Clin. Invest., 96: 1815–1822 (Oct. 1995).
Brooks, P. C. Montgomery, A. M. P., Rosenfeld, M., Reisfeld, R. A., Hu, T., Kller, G., Cheresh D. A., "Integrin αvβ3 Antagonists Promote Tumor Regression by Inducing Apoptosis of Angiogenic Blood Vessels", Cell, 79: 1157–1164 (Dec. 1994).
Brown, S. L., Lundgren, C. H., Nordt, T., Fujii, S., "Stimulation of migration of human aortic smooth muscle cells by vitronectin: implications for atherosclerosis", Cardiovascular Research, 28: 1815–1820 (1994).

* cited by examiner

Primary Examiner—Johann Richter
Assistant Examiner—Paul A. Zucker
(74) Attorney, Agent, or Firm—Jerrie L. Chiu

(57) ABSTRACT

The present invention relates to new phenylserine derivatives as integrin antagonists with a broad spectrum of action having, inter alia, antiosteoporotic, antirestenotic, anticarcinogenic and antiatherosclerotic activity. The present invention moreover relates to the preparation of these compounds and their use for the production of medicaments, and also medicaments comprising them.

7 Claims, No Drawings

PHENYLSERINE DERIVATIVES AS INTEGRIN ANTAGONISTS

RELATED APPLICATIONS

This application claims priority to and the benefit of U.S. Ser. No. 60/211,041, filed Jun. 12, 2000.

The present invention relates to new phenylserine derivatives as integrin antagonists with a broad spectrum of action having, inter alia, antiosteoporotic, antirestenotic, anticarcinogenic and antiatherosclerotic activity. The present invention moreover relates to the preparation of these compounds and their use for the production of medicaments, and also medicaments comprising them.

Integrins are heterodimeric transmembrane proteins found on the surface of cells, which play an important part in the adhesion of the cells to an extracellular matrix. They recognize extracellular glycoproteins such as fibronectin or vitronectin on the extracellular matrix by means of the RGD sequence occurring in these proteins (RGD is the single letter code for the amino acid sequence arginine-glycine-aspartate).

In general, integrins such as, for example, the vitronectin receptor, which is also called the $\alpha_v\beta_3$ receptor, or alternatively the $\alpha_v\beta_5$ receptor or the GpIIb/IIIa receptor play an important part in biological processes such as cell migration and cell-matrix adhesion and thus in diseases in which these processes are crucial steps. Cancer, osteoporosis, arteriosclerosis, restenosis (reoccurrence of stenosis after percutaneous transluminal angioplasty) and opthalmia may be mentioned by way of example.

The $\alpha_v\beta_3$ receptor occurs, for example, in large amounts on growing endothelial cells and makes possible their adhesion to an extracellular matrix. Thus the $\alpha_v\beta_3$ receptor plays an important part in angiogenesis, i.e. the formation of new blood vessels, which is a crucial prerequisite for tumor growth and metastasis formation in carcinoses. Furthermore, it is also responsible for the interaction between osteoclasts, i.e. cells resorbing mineralized tissue, and the bone structure. The first step in the degradation of bone tissue consists in the adhesion of osteoclasts to the bone. This cell-matrix interaction takes place via the $\alpha_v\beta_3$ receptor, which is why the corresponding integrin plays an important part in this process. Osteolytic diseases such as osteoporosis are induced by an inequilibrium between bone formation and bone destruction, i.e. the resorption of bone material caused by accumulation of osteoclasts predominates.

It was possible to show that the blockage of the above-mentioned receptors is an important starting point for the treatment of disorders of this type. If the adhesion of growing endothelial cells to an extracellular matrix is suppressed by blocking their appropriate integrin receptors, for example, by a cyclic peptide or a monoclonal antibody, the endothelial cells die. Therefore angiogenesis does not occur, which leads to a cessation or resolution of the tumor growth (cf., for example, Brooks et al., Cell, Volume 79, 1157–1164, 1994).

Moreover, the invasive properties of tumor cells and thus their capability for metastasis formation are markedly decreased if their $\alpha_v\beta_3$ receptor is blocked by an antibody (Brooks et al., J. Clin. Invest., Volume 96, 1815, 1995).

The degradation of bone tissue can be suppressed by blockage of the $\alpha_v\beta_3$ receptors of the osteoclasts, since these are then unable to accumulate on the bone in order to absorb its substance (WO 98/18461, p. 1, 1. 24 to p. 2,1. 13).

By means of the blockage of the $\alpha_v\beta_3$ receptor on cells of the smooth aorta vascular musculature with the aid of integrin receptor antagonists, the migration of these cells into the neointima and thus angioplasty leading to arteriosclerosis and restenosis can be suppressed (Brown et al., Cardiovascular Res., Volume 28, 1815, 1994).

In recent years, compounds have therefore been sought which act as antagonists of integrin receptors. For example WO 97/24119 discloses victronectin ($\alpha_v\beta_3$) receptor antagonist as antiosteoporosis agents.

It was the object of the present invention to develop compounds which exhibit a high activity as integrin antagonists and in particular against the $\alpha_v\beta_3$ and/or the $\alpha_v\beta_5$ receptor.

The present invention relates to new compounds of the general formula (I)

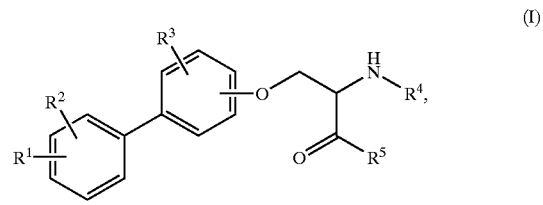

in which

R¹ represents a radical of the formula

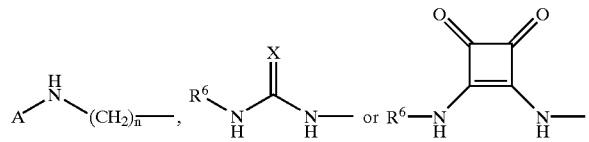

in which

A represents a 5- to 7-membered saturated, partially unsaturated or aromatic heterocycle having up to three identical or different heteroatoms from the group consisting of N, O and/or S, n denotes a number 0, 1, 2, 3 or 4, R⁶ represents hydrogen, $(C_3-C_8)$-cycloalkyl, or straight-chain or branched $(C_1-C_6)$-alkyl, which for its part is optionally substituted by $(C_6-C_{10})$-aryl, by 5- to 6-membered heteroaryl having up to three identical or different heteroatoms from the group consisting of N, O and/or S, or up to several times by halogen, and X denotes O, NH or a radical of the formula =N—CN or =CH—NO₂, R² and R³ are identical or different and denote hydrogen, halogen, $(C_1-C_4)$-alkyl or $(C_1-C_4)$-alkoxy, R⁴ represents $(C_1-C_6)$-alkoxycarbonyl, $(C_6-C_{10})$-arylmethyloxycarbonyl, $(C_1-C_6)$-alkylsulfonyl or $(C_3-C_8)$-cycloalkylsulfonyl, or represents 5- to 6-membered heteroarylsulfonyl having up to three identical or different heteroatoms from the group consisting of N, O and/or S, or $(C_6-C_{10})$-arylsulfonyl, each of which is optionally substituted up to several times identically or differently by halogen, $(C_1-C_4)$-alkyl or $(C_1-C_4)$-alkoxy,
and
$R^5$ denotes hydroxy, $(C_1-C_6)$-alkoxy or benzyloxy,
and their salts.

The compounds according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention. Those particularly preferred are, for example, sodium, potassium, magnesium or calcium salts, and also ammonium salts which are derived from ammonia, or organic amines, such as, for example, ethylamine, di- or triethylamine, ethanolamine, di- or triethanolamine, dicyclohexylamine, dimethyl-aminoethanol, arginine, lysine, ethylenediamine or 2-phenylethylamine.

The present invention also includes ammonium compounds which can be prepared by conversion of the free amines by means of alkylation.

In the context of the present invention, the substituents in general have the following meaning:

$(C_1-C_6)$-alkyl in general represents, depending on the abovementioned substituents, a straight-chain or branched hydrocarbon radical having 1 to 6, preferably 1 to 4 carbon atoms. Examples which may be mentioned are methyl, ethyl, propyl, isopropyl, butyl, isobutyl, pentyl, isopentyl, hexyl, isohexyl.

$(C_1-C_6)$-alkoxycarbonyl can be represented, for example, by the formula

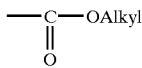

Alkyl here represents a straight-chain or branched hydrocarbon radical having 1 to 6 carbon atoms. Lower alkoxycarbonyl having 1 to 4 carbon atoms in the alkyl moiety is preferred. Examples which may be mentioned are the following alkoxycarbonyl radicals: methoxycarbonyl, ethoxycarbonyl, propoxycarbonyl, isopropoxycarbonyl, tert.-butoxycarbonyl or isobutoxycarbonyl.

$(C_3-C_8)$-cycloalkyl in general represents a cyclic hydrocarbon radical having 3 to 8 carbon atoms. Cyclopropyl, cyclopentyl and cyclohexyl are preferred. Examples which may be mentioned are cyclopentyl, cyclohexyl, cycloheptyl and cyclooctyl.

$(C_6-C_{10})$-aryl in general represents an aromatic radical having 6 to 10 carbon atoms. Preferred aryl radicals are phenyl and naphthyl.

Halogen in the context of the invention represents fluorine, chlorine, bromine and iodine, preferably fluorine, chlorine and bromine.

$(C_1-C_6)$-alkoxy in general represents, depending on the abovementioned substituents, a straight-chain or branched hydrocarbon radical bonded via an oxygen atom and having 1 to 6 carbon atoms. Lower alkoxy having 1 to 4 carbon atoms is preferred. An alkoxy radical having 1 to 3 carbon atoms is particularly preferred. Examples which may be mentioned are methoxy, ethoxy, propoxy, isopropoxy, butoxy, isobutoxy, pentoxy, isopentoxy, hexoxy, isohexoxy.

$(C_1-C_6)$-alkylsulfonyl can be represented by the formula

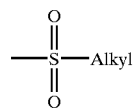

wherein alkyl represents a straight-chain or branched hydrocarbon radical having 1 to 6, preferably 1 to 4 carbon atoms. Examples which may be mentioned are: methylsulfonyl, ethylsulfonyl, propylsulfonyl, isopropylsulfonyl.

$(C_6-C_{10})$-arylsulfonyl can be represented by the formula

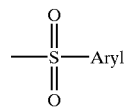

wherein aryl is a $(C_6-C_{10})$-aryl as defined herein.

Heteroarylsulfonyl can be represented by the formula

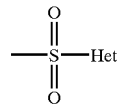

wherein Het represents a 5- or 6-membered heterocycle as defined below.

5- or 7-membered heterocycles in the context of the invention, depending on the abovementioned substituents, in general represent a 5- or 7-membered, preferably 5- to 6-membered saturated, unsaturated or aromatic heterocycle which can contain up to 3 heteroatoms selected from S, N and O and which can optionally also be bound via a nitrogen atom. Examples which may be mentioned are: pyridyl, pyrimidinyl, oxazolyl, thienyl, furyl, pyrrolyl.

The compounds according to the invention can exist in stereoisomeric forms which either behave as image and mirror image (enantiomers), or which do not behave as image and mirror image (diastereomers). The invention relates both to the enantiomers or diastereomers and their respective mixtures. These mixtures of the enantiomers and diastereomers can be separated into the stereoisomerically uniform constituents in a known manner.

Preferred compounds of the general formula (I) according to the invention are those in which $R^1$ represents a radical of the formula

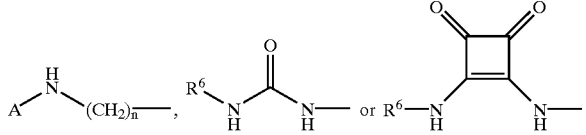

in which
- A represents a 5- to 6-membered aromatic heterocycle having up to three identical of different heteroatoms from the group consisting of N, O and/or S,
- n denotes the number 1 or 2,
and
- $R^6$ represents hydrogen, $(C_3-C_5)$-cycloalkyl, $(C_6-C_{10})$-arylmethyl, 5- to 6-membered heteroarylmethyl having up to three identical of different heteroatoms from the group consisting of N, O and/or S, or straight-chain or branched $(C_1-C_4)$-alkyl, which is optionally substituted up to three times by fluorine or chlorine,
- $R^2$ and $R^3$ are identical or different and denote hydrogen, fluorine, methyl or methoxy,
- $R^4$ represents $(C_1-C_4)$-alkoxycarbonyl, benzyloxycarbonyl, $(C_1-C_4)$-alkylsulfonyl or $(C_3-C_5)$-cycloalkylsulfonyl, or
  represents 5-membered heteroarylsulfonyl having up to three identical or different heteroatoms from the group consisting of N, O and/or S, or phenylsulfonyl, each of which is optionally substituted up to three times identically or differently by fluorine, chlorine, methyl or ethyl,
and
- $R^5$ denotes hydroxy, methoxy, ethoxy or benzyloxy,
and their salts.

Particularly preferred compounds of the general formula (I) according to the invention are those in which
$R^1$ represents a radical of the formula

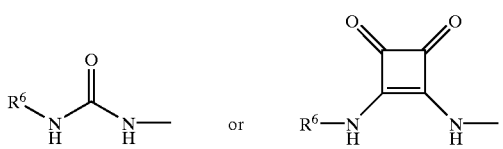

in which
- $R^6$ represents cyclopropyl, cyclobutyl, benzyl, pyridylmethyl, or straight-chain or branched $(C_1-C_3)$-alkyl, which is optionally substituted up to three times by fluorine,
- $R^2$ and $R^3$ each denote hydrogen,
- $R^4$ represents phenylsulfonyl or 1,2- or 1,3-oxazolylsulfonyl, each of which is optionally substituted up to three times identically or differently by fluorine, chlorine or methyl,
and
- $R_5$ denotes hydroxy, methoxy or ethoxy,
and their salts.

Furthermore, a process for the preparation of the compounds of formula (I) was found wherein a compound of formula (II)

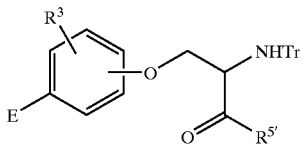

wherein
- $R^3$ has the meaning indicated above,
- $R^{5'}$ has the meaning of $R^5$ as indicated above, except hydroxy,
- Tr represents the triphenyl methane group, and
- E represents halogen, preferably bromine or iodine, is coupled with a compound of formula (III)

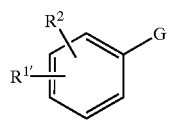

wherein $R^{1'}$ represents amino, nitro or formyl,
- $R^2$ has the meaning indicated above, and
- G represents a tri-$(C_1-C_4)$-alkylstannyl or a di-hydroxy or di-$(C_1-C_4)$-alkoxy boron group, preferably —B(OH)$_2$ in an inert solvent in the presence of a catalyst, to yield compounds of formula (IV)

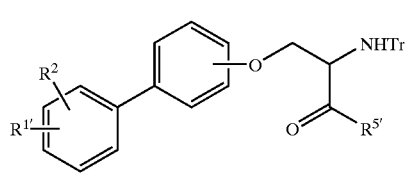

wherein $R^{1'}$, $R^2$, $R^{5'}$ and Tr have the meaning indicated above and from which Tr is cleaved off and the resulting amino group is reacted with a reagent

$R^4$—Y wherein Y represents a leaving group, preferably chlorine, and $R^4$ has the meaning indicated above,
and finally, using standard methods, $R^{1'}$ and $R^{5'}$ are converted into the desired substituents as necessary.

The coupling reaction is preferably a Suzuki or Stille reaction.

Suitable catalysts are palladium compounds such as Pd(PPh$_3$)$_2$Cl$_2$.

The coupling reaction should preferably be run under mild conditions, i.e. at temperatures from 0° to 50° C., preferably at room temperature, to avoid undesired side reactions. It has been found that good yields under mild conditions can be obtained if the ligand triphenylphosphine is exchanged by addition of other ligands, preferably AsPh$_3$.

Furthermore, the coupling reaction may be carried out in the presence of a base. Suitable bases are for example alkaline and alkaline earth metal carbonates, bicarbonates, fluorides, tertiary organic amines, preferably Cs$_2$CO$_3$.

The compounds of formula (II) can be obtained by condensation reaction of compounds of formula (V)

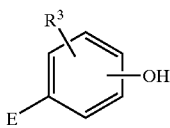

(V)

wherein
R³ and E have the meaning indicated above
with compounds of formula (VI)

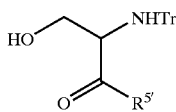

(VI)

wherein R⁵' and Tr have the meaning indicated above.

For the condensation reaction mild reaction conditions are preferred, such as temperatures from 0° C. to 50° C., preferably about room temperature.

It is advantageous to use a suitable condensation agent, preferably standard Mitsunobu reaction conditions, such as the system diethyl azodicarboxylate (DEAD)/triphenylphosphine (PPh₃).

The solvent used should be inert under the reaction conditions, such as for example toluene.

A preferred embodiment of the complete synthesis is exemplified in the following representative synthetic scheme:

Representative Synthetic Scheme

The compounds of the formula (I) according to the invention have a surprisingly wide spectrum of pharmacological action.

The compounds according to the invention exhibit an antagonistic action against integrin inhibitors, in particular the $\alpha_v\beta_3$ receptor or the $\alpha_v\beta_5$ receptor.

They can be used as active compounds in medicaments for the reduction of changes to vascular walls and are employed for the treatment of arterial hypertension and atherosclerosis. Moreover, they can be employed for the treatment of coronary heart disorders, cardiac insufficiency, disorders of brain function, ischemic brain disorders, (peripheral) circulation disorders, microcirculation disorders and thromboses, functional disorders of the kidney and adrenal gland, bronchospastic and vascular system-related disorders of the airways, sodium retention and edemas as well as osteolytic disorders such as osteoporosis, cancer, carcinoses and ophthalmic diseases.

Furthermore, the proliferation and migration of smooth muscle cells plays a decisive part in the occlusion of vessels. The compounds according to the invention are suitable for inhibiting this proliferation and can therefore also be employed for the treatment of restenosis.

The novel active compounds are distinguished pharmacologically by good kinetic parameters. In particular, they have favorable properties with respect to clearance.

The novel active compounds can be converted in a known manner into the customary formulations, such as tablets, coated tablets, pills, granules, aerosols, syrups, emulsions, suspensions and solutions, using inert, nontoxic, pharma

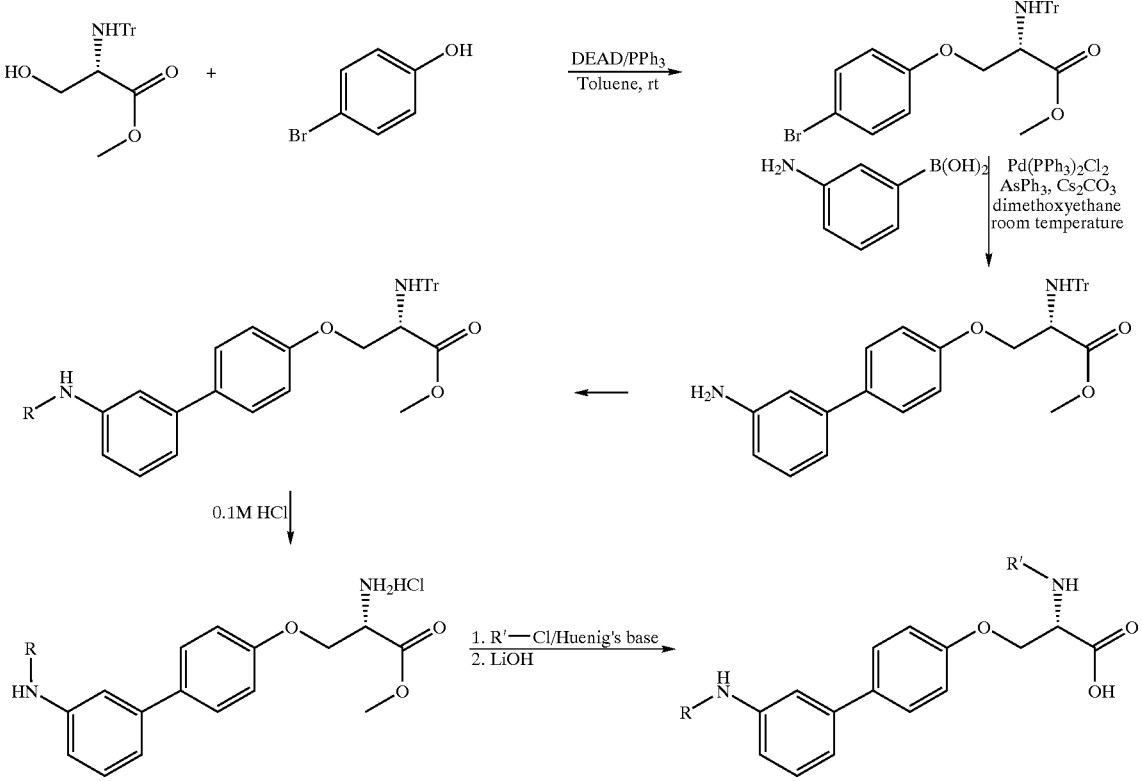

ceutically suitable excipients or solvents. In this case the therapeutically active compound should in each case be present in a concentration of approximately 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, if water is used as a diluent organic solvents can optionally be used as auxiliary solvents.

Administration is carried out in a customary manner, preferably orally or parenterally, in particular perlingually or intravenously.

In the case of parenteral administration, solutions of the active compound using suitable liquid carrier materials can be employed.

In general, it has proven advantageous in the case of intravenous administration to administer amounts from approximately 0.001 to 1 mg/kg, preferably approximately 0.01 to 0.5 mg/kg, of body weight to achieve effective results, and in the case of oral administration the dose is approximately 0.01 to 100 mg/kg, preferably 0.1 to 50 mg/kg, of body weight.

In spite of this, if appropriate, it may be necessary to depart from the amounts mentioned, namely depending on the body weight or the type of application route, on individual behavior toward the medicament, the manner of its formulation and the time or interval at which administration takes place. Thus in some cases it may be adequate to manage with less than the abovementioned minimum amount, while in other cases the upper limits mentioned must be exceeded. In the case of the administration of relatively large amounts, it may be advisable to divide these into several individual doses over the course of the day.

$\alpha_v\beta_3$ inhibitory activity

The substances were tested for their ability to inhibit $\alpha_v\beta_3$/echistatin binding analogously to Kumar C. C., Nie H. M., Rogers G. P., Malkowski M., Maxwell E., Catino J. J. and Armstrong L. (Journal of Pharmacology and Experimental Therapeutics 283(2)(1997)843–853).

$\alpha_v\beta_3$ from human placenta (Smith J. W. and Cheresh, D. A. (1988), J. Biol. Chem. 263, 18726–18732) (1 mg/ml 50 mM tris HCl pH 7.4, 100 mM NaCl, 2 mM $CaCl_2$, 1% and octylglucoside) was diluted with test buffer (50 mM tris-HCl pH 7.4, 100 mM NaCl, 1 mM $CaCl_2$, 1 mM $MgCl_2$, 1 mM $MnCl_2$, 0.1% bovine serum albumin) and 55 µl each of this $\alpha_v\beta_3$ solution were added to the wells of a 96-well microtiter plate (about 0.1–0.3 µg of $\alpha_v\beta_3$ per well). 2 µl of the substances to be tested dissolved in DMSO were then added. 10 µl (40,000 cpm) of $I^{125}$-echistatin per well were then added and the mixture was incubated for 1 hour at room temperature with careful shaking. It was then treated with 100 µg of wheatgerm-coated yttrium silicate beads (Amersham, type RPNQ0011) in 25 µl of distilled water. After 1 hour at room temperature, the cpm values were measured in a scintillation counter. The $K_i$ values were determined in duplicate from concentration series. The non-specific binding was determined in the presence of 0.1 µM unlabeled echistatin or by addition of 5 mM EDTA to the binding mixture.

Results:

| Ex. | $K_i$ |
|-----|-------|
| 20  | 4 nM  |

The present invention is illustrated in greater detail below by working examples.

Experimental Part

EXAMPLE 1

Methyl O-(3-bromophenyl)-N-triphenylmethyl-L-serinate

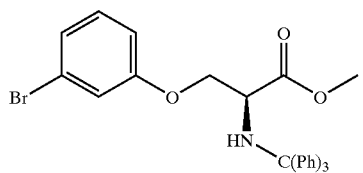

Methyl (2S)-3-hydroxy-2-(triphenylmethylamino) propanoate (5.2 g, 14.4 mmol, 1 equiv; prepared according to Baldwin, J. E.; Spivey, A. C.; Schofield, C. J.; Sweeney, J. B. *Tetrahedron* 1993, 49, 6309) and triphenylphosphine (4.2 g, 15.8 mmol, 1.1 equiv) were dissolved in toluene (25 mL) at rt (room temperature). The reaction mixture was stirred for 30 min followed by addition of 3-bromo phenol (3.2 g, 18.7 mmol, 1.3 equiv) and DEAD (diethylazo dicarboxylate; 2.8 g, 15.8 mmol, 1.1 equiv) at rt. The reaction mixture was stirred at ambient temperature for 15 h while a white precipitate formed. The precipitate was filtered off and the solvents of the filtrate were removed in vacuuo. The remaining crude product was purified by flash chromatography (cyclohexanes/ethyl acetate 95:5) to give a white solid (5.2 g, 67.3%). $^1$H NMR ($CDCl_3$, 200 MHz) δ 7.65–7.55 (m, 4 H); 7.41–7.12 (m, 9H); 6.70 (d, 2H); 4.20 (dd, 1H); 4.00 (dd, 1H); 3.75–3.60 (m, 1H); 3.73 (s, 3H); 2.87 (d, 1H).

EXAMPLE 2

Methyl O-(3'-amino-1,1'-biphenyl-3-yl)-N-triphenylmethyl-L-serinate

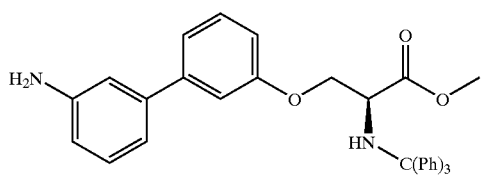

Triphenyl arsine (0.31 g, 1.0 mmol, 0.1 equiv) and dichloro-bis(triphenylphosphine)-palladium(II) (0.35 g, 0.50 mmol, 0.05 equiv) were stirred under an argon atmosphere in DME (dimethoxy ethane; 56 mL) at rt for 30 min. Methyl O-(3-bromophenyl)-N-triphenylmethyl-L-serinate (Example 1) (5.16 g, 10.0 mmol, 1.0 equiv) and 3-amino phenyl boronic acid hemisulfate (2.2 g, 6.0 mmol, 1.2 equiv) were added as solids, followed by a 2M aqueous solution of cesium carbonate (15.0 mL, 30.0 mmol, 3 equiv). The reaction mixture was stirred for 3 h at rt and partioned between toluene and water. The organic layer was separated and dried over sodium sulfate. After filtration and evaporation of the solvents in vacuuo the crude product was purified by chromatography on $SiO_2$ (gradient: toluene to toluene/ethanol 97:3) Yield: 7.3 g, 39.0%. $^1$H NMR ($CDCl_3$, 200 MHz) δ 7.65–7.40 (m, 10H); 7.25–7.12 (m, 11H); 6.97 (d, 2H); 4.70 (dd, 1H); 4.7 (dd, 1H); 3.75–3.65 (m, 3H); 3.24 (s, 3H); 2.90 (d, 1H). MS (DCI/$NH_3$) 546 (M+$NH_4^+$), 529 (M+H); 234 ($CPh_3$).

EXAMPLE 3

Methyl O-(3'-amino-1,1'-biphenyl-4-yl)-N-triphenylmethyl-L-serinate

This compound was prepared from methyl O-(4-bromophenyl)-N-triphenylmethyl-L-serinate and 3-amino phenyl boronic acid hemisulfate in analogy to the procedure of Example 1 and 2.

EXAMPLE 4

Methyl N-triphenylmethyl-O-(3'-{[(propylamino)carbonyl]amino}-1,1'-biphenyl-3-yl)-L-serinate

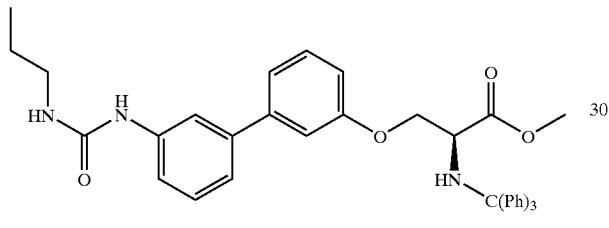

Methyl O-(3'-amino-1,1'-biphenyl-3-yl)-N-triphenylmethyl-L-serinate (Example 2) (250.0 mg, 0.47 mmol, 1 equiv) was dissolved in toluene (5 mL) and treated at rt with n-propyl isocyanate (402.5 mg, 4.73 mmol, 10 equiv) and DABCO (1,4-diazabicyclo[2,2,2]octane) (5.3 mg, 0.05 mmol, 0.1 equiv). The reaction mixture was stirred at rt for 14 h and then partitioned between toluene and sat. aqueous $NH_4Cl$ solution. The organic layer was separated and dried over $NaSO_4$ and the solvents were removed in vacuuo. The crude product was titurated with petroleum ether to give a yellow solid. Yield 210.0 mg, 72.4%. $^1$H NMR ($CDCl_3$, 200 MHz) δ 7.65–7.50 (m, 9H); 7.40–7.15 (m, 12H); 6.95 (d, 2H); 5.19–4.98 (m, 1H); 4.25 (dd, 1H); 4.03 (dd, 1H); 3.38–3.02 (m, 4H); 2.88 (d, 1H); 1.65–1.45 (m, 2H); 0.90 (t, 3H). MS (EI) 614 (M+H), 243 ($CPh_3$).

EXAMPLE 5

Methyl O-(3'-{[(propylamino)carbonyl]amino}-1,1'-biphenyl-4-yl)-N-triphenylmeth-yl-L-serinate This compound was prepared from Example 3 in analogy to the procedure of Example 4.

EXAMPLE 6

Methyl O-(3'-{[(propylamino)carbonyl]amino}-1,1'-biphenyl-3-yl)-L-serinate hydrochloride

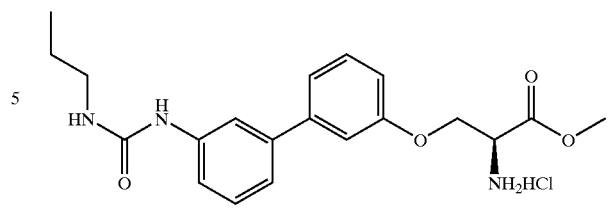

Methyl N-triphenylmethyl-O-(3'-{[(propylamino)carbonyl]amino}-1,1'-biphenyl-3-yl)-L-serinate (Example 4) (291.2 mg, 0.48 mmol, 1 equiv) was dissolved in MeOH and treated with a 1 M solution of HCl in diethylether at rt. The solution was stirred for 2 h at rt and then the solvents were removed in vacuuo. The crude product was titurated with ether to give a yellow precipitate which was filtered off and dried in vacuo. Yield 195.0 mg, 99%. $^1$H NMR (DMSO, 200 MHz) δ 8.85 (brs, 2H); 7.82 (s, 1H); 7.55 (d, 2H); 7.49–7.22 (m, 3H); 7.05 (d, 2H); 4.85–4.55 (m, 1H); 4.49–4.29 (m, 2H); 3.80 (s, 3H); 2.92 (dd, 1H); 1.60–1.29 (m, 3H); 0.96 (t, 3H).

EXAMPLE 7

Methyl N-(ethoxycarbonyl)-O-(3'-{[(propylamino)carbonyl]amino}-1,1'-biphenyl-3-yl)-L-serinate

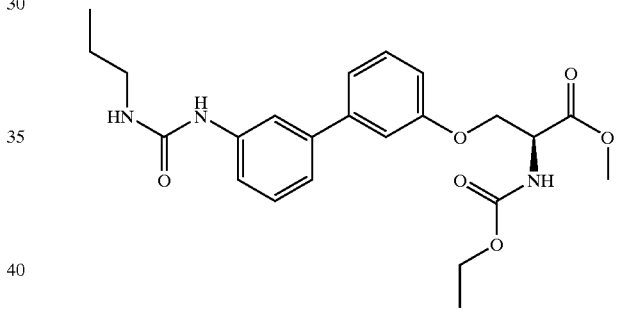

The compound of Example 6 (256.0 mg, 0.63 mmol, 1 equiv) was suspended in THF (3 mL) and cooled to 0° C. Ethyl chloroformiate (88.5 mg, 0.82 mmol, 1.3 equiv) was added dropwise followed by N,N diisopropylethylamine (234.3 mg, 1.88 mmol, 3 equiv). The reaction mixture was allowed to warm to room temperature and stirred for one hour. It was worked up by addition of sat. aqueous $NH_4Cl$ soln. and ethyl acetate. The phases were separated and the organic layer was dried over $NaSO_4$. After filtration and evaporation of the solvents the crude product was purified by chromatography ($SiO_2$ CH/EtOAc 90:10). Yield 210.0 mg, 75.4% of a white solid. $^1$H NMR ($CDCl_3$, 300 MHz) δ 7.50 (s, 1H); 7.39–7.25 (m, 3H); 7.21 (d, 1H), 7.12 (d, 1H); 7.05 (s, 1H); 6.90 (brs, 1H); 6.81 (d, 1H); 5.80 (d, 1H); 5.10 (m, 1H); 4.75–4.65 (m, 1H); 4.42 (dd, 1H); 4.25 (dd, 1H); 4.20–4.10 (m, 2H); 3.79 (s, 3H); 3.20 (dd, 2H); 1.52 (sext, 2H); 1.22 (t, 3H); 0.95 (t, 3H). MS (DCI/$NH_3$) 461 (M+$NH_4$), 444 (M+H).

EXAMPLE 8

N-(Ethoxycarbonyl)-O-(3'-{[(propylamino)carbonyl]amino}-1,1'-biphenyl-3-yl)-L-serine

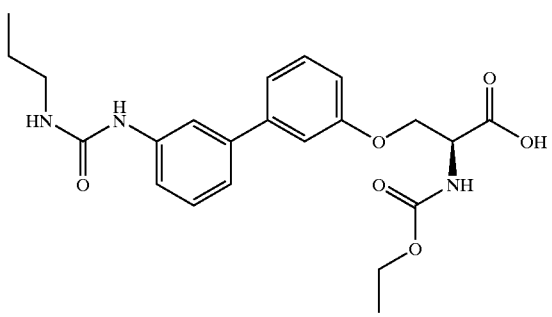

The compound of Example 7 (100.0 mg, 0.23 mmol, 1 equiv) was dissolved in THF/MeOH/H$_2$O (3:1:1 2.3 mL) and the solution was cooled to 0° C. followed by addition of solid lithium hydroxide (5.4 mg, 0.23 mmol, 1 equiv). The reaction mixture was allowed to reach rt and stirred for 1 hour. It was acidified with 0.1 M aqueous HCl solution to pH 3 and extracted three times with ethyl acetate. The combined organic extracts were dried over Na$_2$SO$_4$ and the solvents were removed under reduced pressure and the remaining crude product was purified by chromatography (SiO$_2$; toluene/EtOH/AcOH 95:4:1). Yield 23.7 mg, 24.5%. $^1$H NMR (DMSO; 200 MHz) δ 13.05 (brs, 1H); 8.59 (s, 1H); 7.72 (s, 1H); 7.05 (d, 1H); 7.41–7.22 (m, 3H); 7.17–7.03 (m, 3H); 6.91 (d, 1H); 6.22 (dd, 1H); 4.49–4.81 (m, 1H); 4.30–4.19 (m, 2H); 4.0 (q, 2H); 3.04 (q, 2H); 1.49 (sextett, 2H); 1.19 (t, 3H); 0.94 (t, 3H). MS (EI) 430 (M+H), 345, 210.

EXAMPLE 9
Methyl N-triphenylmethyl-O-[3'-({[(2-pyridinylmethyl) amino]carbonyl}amino)-1,1'-biphenyl-3-yl]-L-serinate

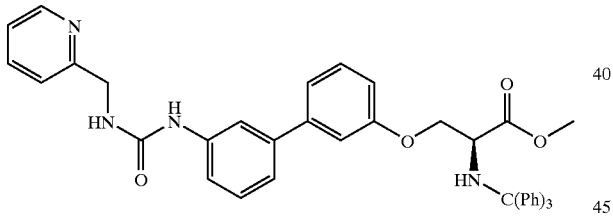

The compound of Example 2 (2.30 g, 4.36 mmol, 1 equiv) was dissolved in THF (25 mL). Diisopropyl ethyl amine (0.68 g, 5.23 mmol, 1.2 equiv) was added followed by addition of 4-nitrophenyl chloroformiate (1.09 g, 5.23 mmol, 1.2 equiv). The reaction mixture was stirred for 1 h at 20° C. and then picloyl amine (0.57 g, 5.23 mmol, 1.2 equiv) was added at room temperature. The reaction was stirred for 12 h and then the solvent was removed under reduced pressure. The residual oil was taken up in ethyl acetate and washed with water. The phases were separated and the aqueous phase was rextracted with ethyl acetate. The combined organic extracts were washed with saturated aqueous NaHCO$_3$ solution and water and then dried over Na$_2$SO$_4$. After filtration the solvents were removed in vacuuo. The remaining crude product was purified by chromatography (SiO$_2$, CH/EtOAc gradient 30:70 to 20:80). Yield 1.43 g, 49.5% of a yellow solid. $^1$H NMR (CDCl$_3$, 400 MHz) δ 8.88 (s, 1H); 8.50 (s, 1H); 7.80–7.68 (m, 3H); 7.51–7.40 (m, 8H); 7.39–7.20 (m, 8H); 7.20–7.11 (m, 6H); 7.05 (s, 1H); 6.89–6.67 (m, 2H); 4.45 (s, 2H); 4.29–4.20 (m, 1H); 3.69–3.49 (m, 1H); 3.30 (s, 3H); 3.27 (s, 2H); 3.18 (d, 1H-NH). MS (EI) 663 (M+H), 243 (CPh$_3$).

EXAMPLE 10
Methyl O-[3'-({[(2-pyridinylmethyl)amino] carbonyl}amino)-1,1'-biphenyl-3-yl]-L-serinate hydrochloride

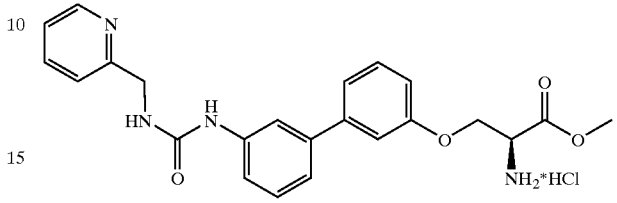

The compound of Example 9 (1369,8 mg, 2.07 mmol, 1 equiv) was dissolved in dioxane (4 mL) and treated with a 1M solution of hydrochloric acid in dioxane (4.5 mL, 4.5 mmol, 2.2 equiv) at room temperature. The reaction mixture was stirred for 3.5 h at ambient temperature. The solvents were removed under reduced pressure and the crude product was titurated with diethylether. The white precipitate was filtered off and dried in vacuuo. Yield 615.4 mg, 65.2% of a white solid. $^1$H NMR (DMSO, 200 MHz) δ 9.69 (s, 1H-NH); 8.95 (s, 2H); 8.79 (d, 1H); 8.52–8.38 (m, 1H); 7.99–7.72 (m, 3H); 7.55–7.32 (m, 4H); 7.25–7.17 (m, 3H); 7.02 (d, 1H); 4.82–4.59 (m, 2H); 4.51–4.40 (m, 1H); 3.80 (s, 3H), 2.55 (s, 2H). MS (ESI) 443 (M+Na), 421 (M+H).

EXAMPLE 11
Methyl N-(ethoxycarbonyl)-O-[3'-({[(2-pyridinylmethyl) amino]carbonyl}amino)-1,1'-biphenyl -3-yl]-L-serinate

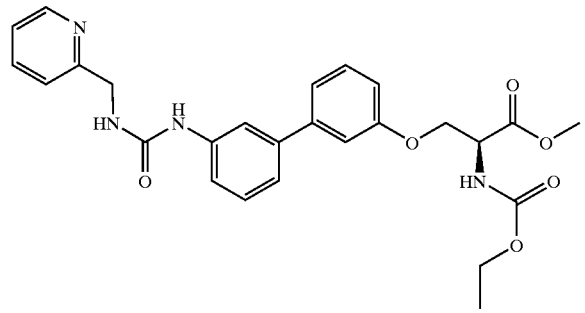

The compound of Example 10 (200.0 mg, 0.44 mmol, 1 equiv) and ethyl chloroformate (61.5 mg, 0.57 mmol, 1.3 equiv) was suspended in THF (3 mL). The mixture was cooled to 0° C. and N,N-diisopropylamine (169.7 mg, 1.3 mmol, 3 equiv) was added dropwise. The reaction mixture was allowed to reach room temperature and stirred for 1 hour. It was partitioned between saturated aqueous NH$_4$Cl solution and ethyl acetate. The phases were separated and the organic layer was dried over Na$_2$SO$_4$. After removal of the solvents in vacuuo the crude product was purified by chromatography. (SiO$_2$, EtOAc). Yield 125. 8 mg, 58.3%. $^1$H NMR (DMSO, 300 MHz) δ 8.88 (s, 1H); 8.51 (d, 1H); 7.85–7.79 (m, 3H); 7.45–7.22 (m, 5H); 7.20 (d, 1H); 7.12 (s, 1H); 6.93 (d, 1H); 6.79 (dd, 1H); 4.61–4.50 (m, 1H); 4.42 (d, 2H); 4.38–4.21 (m, 2H); 4.05 (q, 2H); 3.70 (s, 3H); 1.15 (t, 3H). MS (EI) 493 (M+H).

EXAMPLE 12
Methyl N-(ethoxycarbonyl)-O-[3'-({[(2-pyridinylmethyl)amino]carbonyl}amino)-1,1'-biphenyl-3-yl]-L-serine

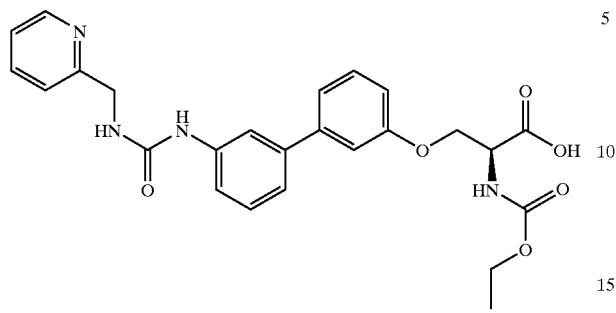

The compound of Example 11 (56.0 mg, 0.11 mmol, 1 equiv) was dissolved in THF/MeOH/H$_2$O (3:1:1; 1.2 mL). Solid lithium hydroxide (2.8 mg, 0.11 mmol, 1 equiv) was added at 0° C. The reaction mixture was allowed to stirr for 1 hour at 0° C. It was then acidified with 0.1N aqueous HCl solution to pH 3 and extracted three times with ethyl acetate. The combined organic extracts were dried over Na$_2$SO$_4$. After removal of the solvents under reduced pressure the crude product was purified by chromatography (SiO$_2$, toluene/EtOH/HOAc 85:14:1). Yield 16.3 mg, 30%. $^1$H NMR (DMSO, 300 MHz) δ 8.54 (s, 1H); 7.80 (m, 2H); 7.49–7.23 (m, 7H); 7.20 (m, 1H), 7.03 (m, 1H); 6.69–6.50 (m, 1H); 4.47 (d, 2H); 4.30–4.19 (m, 1H); 4.12–3.89 (m, 3H); 1.09 (t, 3H). MS (EI) 479 (M+H).

EXAMPLE 13
Methyl O-{3'-[(2-ethoxy-3,4-dioxo-1-cyclobutene-1-yl)amino]-1,1'-biphenyl-4-yl}-N-triphenylmethyl-L-serinate

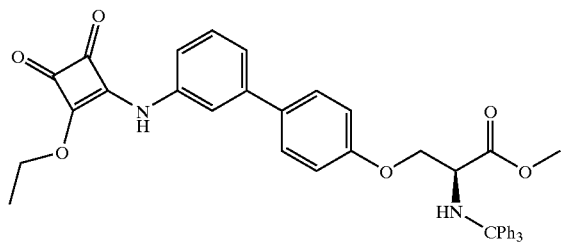

The compound of Example 3 (1.50 g, 2.8 mmol, 1 equiv) was dissolved in 3,4-diethoxy-3 cyclobutene-1,2-dione (2.1 mL, 14.2 mmol, 5 equiv). The reaction mixture was stirred at 60–70° C. for 1 h. It was then allowed to cool to rt and diluted with CH$_2$Cl$_2$/EtOAc 9:1 (12 mL). The solution was filtered over a pad of silica gel and eluted with CH$_2$Cl$_2$/EtOAc 9:1. Unreacted 3,4-diethoxy-3-cyclobutene-1,2-dion eluted first followed by the title compound. Yield 0.68 g, 36.7%. $^1$H NMR (CDCl$_3$, 7.72–7.51 (m, 8H); 7.48–7.32 (m, 3H); 7.29–7.03 (m, 10H); 6.94 (d, 2H); 4.94 (q, 2H); 4.29 (dd, 1H); 4.14 (dd, 1H); 3.85–3.69 (m, 1H); 3.23 (s, 3H); 2.90 (d, 1H); 1.55 (t, 3H). MS (ESI) 675 (M+Na), 653 (M+H), 243 (CPh$_3$).

EXAMPLE 14
Methyl O-(3'-{[2-(cyclopropylamino)-3,4-dioxo-1-cyclobuten-1-yl]amino}-1,1'-bi-phenyl-4-yl)-N-triphenyl-methyl-L-serinate

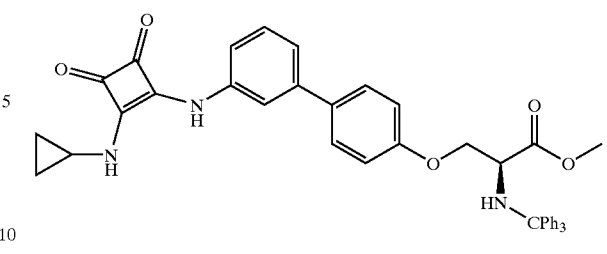

The compound of Example 13 (670.0 mg, 1.0 mmol, 1 equiv) was dissolved in dioxane (5.2 mL) at rt. Cyclopropyl amine (645.0 mg, 1.1 mmol, 1.1 equiv) was added and the reaction mixture was warmed to 50° C. for 30 min. The mixture was cooled to rt again and the solvent was removed under reduced pressure. The remaining crude product was purified by chromatography (SiO$_2$; CH$_2$Cl$_2$/EtOAc 70:30). Yield 397 mg, 58.2%.

$^1$H NMR (CDCl$_3$, 200 MHz) δ 7.61–7.42 (m, 4H); 7.33–7.05 (m, 18H); 6.99–6.87 (m, 1H); 4.3 (dd, 1H); 4.20–3.91 (m, 2H); 3.32–3.17 (m, 1H); 3.75 (s, 3H); 0.91–0.67 (m, 4H). MS (ESI) 686 (M+Na), 243 (CPh$_3$).

EXAMPLE 15
Methyl O-(3'-{[2-(cyclopropylamino)-3,4-dioxo-1-cyclobuten-1-yl]amino}-1,1'-bi-phenyl-4-yl)-L-serinate hydro-chloride

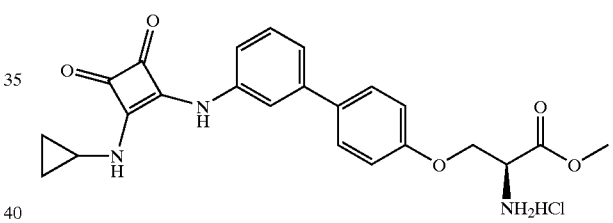

The compound of Example 14 (380.0 mg, 0.57 mmol, 1 equiv) was dissolved in MeOH (5 mL) and treated with HCl in dioxane at rt. The reaction mixture was stirred for two hours at ambient temperature. It was partitioned between H$_2$O and CH$_2$Cl$_2$. The aqueous layer was collected and the solvent was removed under reduced pressure to give the title compound as a white solid. Yield 301 mg, 25.4%. $^1$H NMR (DMSO, 200 MHz) δ 7.94 (s, 1H); 7.79–7.43 (m, 4H); 7.39–7.30 (m, 1H); 7.21–7.15 (m, 1H); 7.17–7.01 (m, 2H); 4.72 (s(2H); 4.55–4.3 (m, 2H); 4.32–4.05 (m, 1H); 3.75 (s, 3H); 3.17–3.00 (m, 1H); 0.87–0.57 (m, 4H). MS (ESI) 422 (M+H).

EXAMPLE 16
Methyl O-(3'-{[(propylamino)carbonyl]amino}-1,1'-biphenyl-4-yl)-L-serinate hydro-chloride This compound was prepared from Example 5 in analogy to the procedure of Example 15.

EXAMPLE 17
Methyl O-(3'-{[2-(cyclopropylamino)-3,4-dioxo-1-cyclobuten-1-yl]amino}-1,1'-bi-phenyl-4-yl)-N-(ethoxycarbonyl)-L-serinate

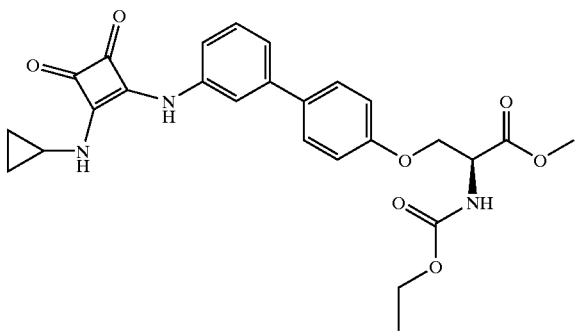

The compound of Example 15 (97.0 mg, 0.2 mmol, 1 equiv) and ethyl chloroformate (29.8 mg, 0.3 mmol, 1.3 equiv) were suspended in THF (2 mL) and cooled to 0° C. Ethyldiisopropyl amine (82.1 mg, 0.6 mmol, 3 equiv) was added dropwise and the reaction mixture was allowed to reach rt. It was stirred for 1 hour at ambient temperature. Ethyl acetate and saturated aqueous NH$_4$Cl solution were added and the phases were separated. The aqueous layer was extracted three times with ethyl acetate and the combined organic extracts were dried over Na$_2$SO$_4$. After removal of the solvents under reduced pressure the crude product was purified by chromatography (SiO$_2$, gradient CH/EtOAc 6:4 to EtOAc 100%). Yield 39.0 mg, 37.3%. $^1$H NMR (CDCl$_3$, 400 MHz) δ 7.61–7.55 (m, 1H); 7.52–7.49 (m, 2H); 7.31-7.18 (m, 2H); 7.09–6.96 (m, 1H); 6.82 (d, 2H); 5.71 (d, 1H); 4.79–4.64 (m, 1H); 4.34-4.29 (m, 1H); 4.19–4.02 (m, 4H); 3.75 (s, 3H); 3.19–3.06 (m, 1H); 1.23 (t, 3H); 0.89-0.75 (m, 2 H); 0.76–0.68 (m, 2H). MS (EI) 494 (M+H).

EXAMPLE 18
O-(3'-{[2-(cyclopropylamino)-3,4-dioxo-1-cyclobuten-1-yl]amino}-1,1'-biphenyl-4-yl)-N-(ethoxycarbonyl)-L-serine

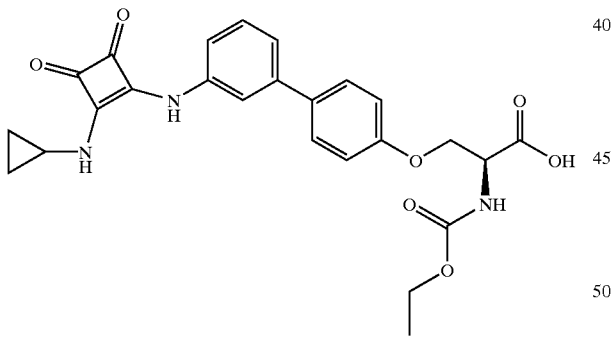

The compound of Example 17 (22.0 mg, 0.04 mmol, 1 equiv) was dissolved in THF/MeOH/H$_2$O 3:1:1 (1 mL) and cooled to 0° C. Solid lithium hydroxide (5.3 mg, 0.22 mol, 5 equiv) was added and the reaction mixture was stirred for two hours at 0° C. The solvents were removed under reduced pressure and the residue was taken up with H$_2$O (2 mL). The resulting solution was acidified with 0.1 N HCl to pH 3 and stirred for 30 min., while a white precipitate was formed. The precipitated title compound was isolated by filtration and dried under vacuum. Yield 15.0 mg, 70.2%. $^1$H NMR (DMSO, 200 MHz) δ 10.45 (brs, 1H); 9.65 (s, 1H); 8.61 (s, 1H); 7.90–7.71 (m, 1H); 7.65–7.55 (m, 1H); 7.59–7.43 (m, 1H); 7.39–7.17 (m, 3H); 7.02 (d, 1H); 6.84 (d, 1H); 4.49–4.38 (m, 1H); 4.30–4.19 (m, 1H); 4.0 (q, 2H); 3.19–3.02 (m, 1H); 1.17 (t, 3H); 0.85–0.65 (m, 4H). MS (EI) 502 (M+Na), 480 (M+H), 321.

EXAMPLE 19
Methyl N-(mesitylsulfonyl)-O-(3'-{[(propylamino)carbonyl]amino}-1,1'-biphenyl-4-yl)-L-serinate

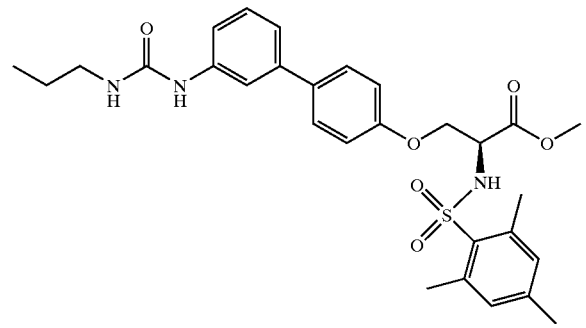

The compound of Example 16 (200.0 mg, 0.49 mmol, 1 equiv) and mesityl-sulfonylchloride (128.7 mg, 0.58 mmol, 1.2 equiv) were suspended in CH$_2$Cl$_2$ and diisopropyl ethyl amine (0.20 mL, 1.01 mmol, 2.2 equiv) was added dropwise at rt, resulting in a clear solution of the reaction mixture. The reaction was stirred for 24 h at ambient temperature and then partioned between toluene and saturated aqueous NH$_4$Cl solution. The organic layer was separated and dried over NaSO$_4$. After removal of the solvents under reduced pressure the crude product was purified by chromatography (SiO$_2$; gradient CH/EtOAc 1:1 to EtOAc 100%). Yield 107.0 mg, 39.4%. $^1$H NMR (DMSO, 200 MHz) δ 8.48 (s, 2H); 7.70 (s, 1H); 7.49 (d, 2H); 7.22 (d, 2H); 7.11–7.03 (m, 1H); 6.98 (s, 2H); 6.80 (d, 2H); 6.19–6.00 (m, 1H); 4.12–3.97 (m, 3H); 3.50 (s, 3H); 3.12–2.90 (m, 1H); 2.50 (s, 6H); 2.20 (s, 3H); 1.50–1.31 (m, 2H); 0.94 (t, 3H). MS (ESI) 554 (M+H).

EXAMPLE 20
N-(Mesitylsulfonyl)-O-(3'-{[(propylamino)carbonyl]amino}-1,1'-biphenyl-4-yl)-L-serine

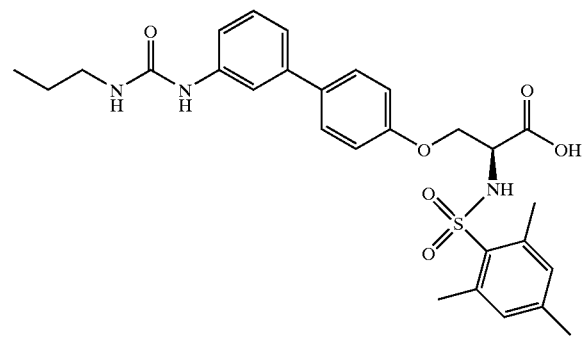

The compound of Example 19 (60.0 mg, 0.11, 1 equiv) was dissolved in isopropanol (3.0 mL) and treated with a 1 M aqueous solution of NaOH (1 mL). The reaction mixture was warmed to 60° C. and stirred for 4 hours. It was acidified with a 0.1 M aqueous solution of HCl to pH 2 and cooled to 4° C. overnight. The white precipitate of the title compound was filtered off and dried under vacuum. Yield 30.0 mg, 51.3%. $^1$H NMR (DMSO; 200 MHz) δ 13.99

(broad s, 1H); 8.50 (s, 2H); 7.71 (s, 1H); 7.49 (d, 2H); 7.25 (d, 2H); 7.15–7.12 (m, 1H); 7.00 (s, 2H); 6.88 (d, 2H); 6.23-6.09 (m, 1H); 4.19–4.03 (m, 3H); 3.21–2.93 (m, 1H); 2.59 (s, 6H); 2.21 (3H), 1.43 (quin, 2H); 0.97 (t, 3H). MS (ESI) 540 (M+H).

What is claimed is:

1. Compounds of the general formula (I)

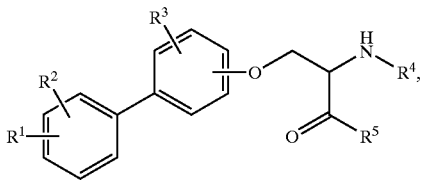

(I)

in which

R$^1$ represents a radical of the formula

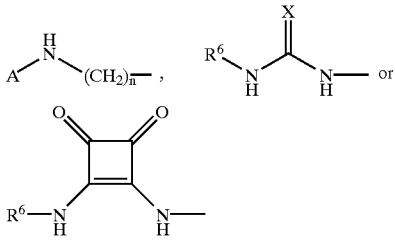

in which

A represents a 5- to 7-membered saturated, partially unsaturated or aromatic heterocycle having up to three identical or different heteroatoms from the group consisting of N, O and S, n denotes a number 0, 1, 2, 3 or 4, R$^6$ represents hydrogen, (C$_3$–C$_8$)-cycloalkyl, or straight-chain or branched (C$_1$–C$_6$)-alkyl, which for its part is optionally substituted by (C$_6$–C$_{10}$)-aryl, by 5- to 6-membered heteroaryl having up to three identical or different heteroatoms from the group consisting of N, O and S, or up to several times by halogen, and X denotes O, NH or a radical of the formula =N—CN or =CH—NO$_2$, R$^2$ and R$^3$ are identical or different and denote hydrogen, halogen, (C$_1$–C$_4$)-alkyl or (C$_1$–C$_4$)-alkoxy, R$^4$ represents (C$_1$–C$_6$)-alkoxycarbonyl, (C$_6$–C$_{10}$)-arylmethyloxycarbonyl, (C$_{1-C6}$)-alkylsulfonyl or (C$_3$–C$_8$)-cycloalkylsulfonyl, or represents 5- to 6-membered heteroarylsulfonyl having up to three identical or different heteroatoms from the group consisting of N, O and S, or (C$_6$–C$_{10}$)-arylsulfonyl, each of which is optionally substituted up to three times identically or differently by halogen, (C$_1$–C$_4$)-alkyl or (C$_1$–C$_4$)- alkoxy, R$^5$ denotes hydroxy, (C$_1$–C$_6$)-alkoxy or benzyloxy, and their salts.

2. Compounds of the formula (I) according to claim 1, in which

R$^1$ represents a radical of the formula

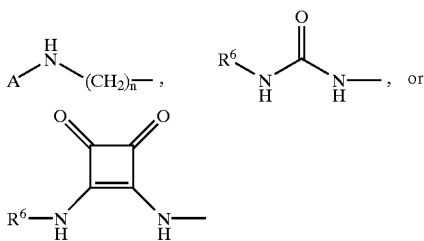

in which

A represents a 5- to 6-membered aromatic heterocycle having up to three identical of different heteroatoms from the group consisting of N, O and S, n denotes the number 1 or 2, and R$^6$ represents hydrogen, (C$_3$–C$_5$)-cycloalkyl, (C$_6$–C$_{10}$)-arylmethyl, 5- to 6-membered heteroarylmethyl having up to three identical of different heteroatoms from the group consisting of N, O and S, or straight-chain or branched (C$_1$–C$_4$)-alkyl, which is optionally substituted up to three times by fluorine or chlorine, R$^2$ and R$^3$ are identical or different and denote hydrogen, fluorine, methyl or methoxy, R$^4$ represents (C$_1$–C$_4$)-alkoxycarbonyl, benzyloxycarbonyl, (C$_1$–C$_4$)-alkyl- sulfonyl or (C$_{3-C5}$)-cycloalkylsulfonyl, or represents 5-membered heteroarylsulfonyl having up to three identical or different heteroatoms from the group consisting of N, O and S, or phenylsulfonyl, each of which is optionally substituted up to three times identically or differently by fluorine, chlorine, methyl or ethyl, R$^5$ denotes hydroxy, methoxy, ethoxy or benzyloxy, and their salts.

3. Compounds of the general formula (I) according to claim 1, in which

R$^1$ represents a radical of the formula

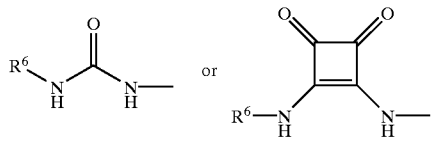

in which

R$^6$ represents cyclopropyl, cyclobutyl, benzyl, pyridylmethyl, or straight-chain or branched (C$_1$ –C$_3$)-alkyl, which is optionally substituted up to three times by fluorine, R$_2$ and R$_3$ each denote hydrogen, R$^4$ represents phenylsulfonyl or 1,2- or 1,3-oxazolylsulfonyl, each of which is optionally substituted up to three times identically or differently by fluorine, chlorine or methyl, R$^5$ denotes hydroxy, methoxy or ethoxy, and their salts.

4. A process for the preparation of compounds of formula (I), comprising (a) coupling a compound of formula (II)

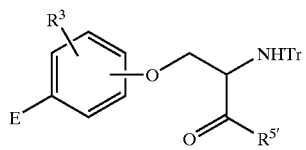
(II)

wherein $R^3$ has the meaning indicated above in claim 1, $R^{5'}$ has the meaning of $R^5$ as indicated above in claim 1, except hydroxy, Tr represents the triphenyl methane group, and E represents halogen, with a compound of formula (III)

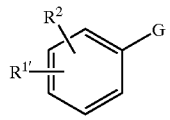
(III)

wherein $R^{1'}$ represents amino, nitro or formyl, $R^2$ has the meaning indicated above in claim 1, and G represents a tri-$(C_1-C_4)$-alkylstannyl or a di-hydroxy or di-$(C_1-C_4)$-alkoxy boron group, preferably —$B(OH)_2$ in an inert solvent in the presence of a catalyst, to yield compounds of formula (IV)

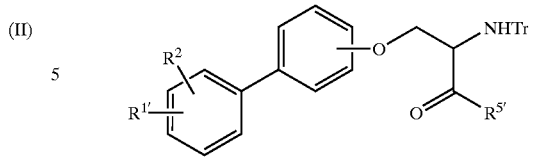
(IV)

wherein $R^{1'}$, $R^2$, $R^{3'}$ and Tr have the meaning indicated above, (b) cleaving Tr off to provide an amino group, (c) reacting the resulting amino group with a reagent $R^4$—Y wherein Y represents a leaving group, and $R^4$ has the meaning indicated above in claim 1, and (d) converting $R^{1'}$ and $R^{5'}$ into the desired substituents $R^1$ and $R^5$, which have the meanings indicated above in claim 1.

5. A method of treating or preventing osteoporosis, restenosis, and atherosclerotic diseases, comprising administering to a mammal an effective amount of a compound of formula (I) according to claim 1.

6. Pharmaceutical compositions comprising a compound of formula (I) according to claim 1 and a pharmaceutically suitable excipient and/or solvent.

7. A method of treating cancer, comprising administering to a mammal an effective amount of a compound of formula (I) according to claim 1.

* * * * *